(12) United States Patent
St. Anne et al.

(10) Patent No.: US 10,335,343 B2
(45) Date of Patent: *Jul. 2, 2019

(54) METHOD AND DEVICE FOR TREATING FEMALE PELVIC NERVE DYSFUNCTION

(71) Applicant: ParaPatch, Inc., Campbell, CA (US)

(72) Inventors: Cora St. Anne, Inglewood, CA (US); Theodore V. Benderev, San Juan Capistrano, CA (US)

(73) Assignee: ParaPatch, Inc., Campbell, CA (US)

( * ) Notice: Subject to any disclaimer, the term of this patent is extended or adjusted under 35 U.S.C. 154(b) by 138 days.

This patent is subject to a terminal disclaimer.

(21) Appl. No.: 15/230,304

(22) Filed: Aug. 5, 2016

(65) Prior Publication Data

US 2016/0338902 A1 Nov. 24, 2016

Related U.S. Application Data

(63) Continuation of application No. 13/776,930, filed on Feb. 26, 2013, now Pat. No. 9,408,683, which is a
(Continued)

(51) Int. Cl.
| | |
|---|---|
| *A61F 5/48* | (2006.01) |
| *A61H 19/00* | (2006.01) |
| *A61N 1/36* | (2006.01) |
| *A61F 2/00* | (2006.01) |
| *A61F 15/00* | (2006.01) |

(Continued)

(52) U.S. Cl.
CPC ........... *A61H 19/34* (2013.01); *A61F 2/0009* (2013.01); *A61F 2/0022* (2013.01); *A61F 13/02* (2013.01); *A61F 13/472* (2013.01); *A61F 15/002* (2013.01); *A61N 1/36007* (2013.01); *A61N 1/36014* (2013.01); *A61F 2013/15121* (2013.01); *A61F 2210/0014* (2013.01); *A61F 2250/0036* (2013.01); *A61F 2250/0078* (2013.01); *A61H 19/50* (2013.01); *A61H 2201/165* (2013.01); *A61H 2201/1688* (2013.01)

(58) Field of Classification Search
CPC ........ A61F 2/0054; A61F 5/48; A61F 2/0009; A61F 2/0022; A61F 2/0013; A61F 6/04; A61F 5/41; A61F 6/24; A61F 6/22; A61F 6/20; A61F 2006/047; A61F 2006/048; A61F 5/453; A61F 13/471; A61B 17/11; A61H 19/34

See application file for complete search history.

(56) References Cited

U.S. PATENT DOCUMENTS

| | | |
|---|---|---|
| 3,646,616 A | 3/1972 | Keshin |
| 3,762,415 A | 10/1973 | Morrison |

(Continued)

OTHER PUBLICATIONS

U.S. Appl. No. 15/349,783, filed Nov. 11, 2016, St. Anne et al.
(Continued)

*Primary Examiner* — Ophelia A Hawthorne
(74) *Attorney, Agent, or Firm* — Knobbe, Martens, Olson & Bear, LLP

(57) ABSTRACT

A method and devices for stimulating visceral pelvic or somatic nerves or their pathways of a female person suffering from a pelvic condition of nerve dysfunction in which non-electrical, external physical stimulation is applied to the clitoral region of the person.

20 Claims, 4 Drawing Sheets

Related U.S. Application Data continuation-in-part of application No. 12/999,114, filed as application No. PCT/US2010/033349 on May 3, 2010, now Pat. No. 8,684,008.

(60) Provisional application No. 61/181,556, filed on May 27, 2009.

(51) Int. Cl.
*A61F 13/02* (2006.01)
*A61F 13/472* (2006.01)
*A61F 13/15* (2006.01)

(56) References Cited

U.S. PATENT DOCUMENTS

| | | |
|---|---|---|
| 3,789,828 A | 5/1974 | Schulte |
| 3,905,372 A | 9/1975 | Denkinger |
| 3,911,173 A | 10/1975 | Sprague, Jr. |
| 3,929,135 A | 12/1975 | Thompson |
| 4,191,609 A | 3/1980 | Trokhan |
| 4,324,246 A | 4/1982 | Mullane et al. |
| 4,342,314 A | 8/1982 | Radel et al. |
| 4,367,732 A | 1/1983 | Poulsen et al. |
| 4,463,045 A | 7/1984 | Ahr et al. |
| 4,486,193 A | 12/1984 | Shaw et al. |
| 4,573,986 A | 3/1986 | Minetola et al. |
| 4,610,678 A | 9/1986 | Weisman et al. |
| 4,782,535 A | 11/1988 | Bjornberg et al. |
| 4,785,996 A | 11/1988 | Ziecker et al. |
| 4,822,347 A | 4/1989 | MacDougall |
| 4,834,735 A | 5/1989 | Alemany et al. |
| 4,842,666 A | 6/1989 | Werenicz |
| 4,846,819 A | 7/1989 | Welch |
| 4,850,986 A | 7/1989 | Temple |
| 4,875,898 A | 10/1989 | Eakin |
| 4,892,535 A | 1/1990 | Bjornberg et al. |
| 4,917,697 A | 4/1990 | Osborn, III et al. |
| 4,920,986 A | 5/1990 | Biswas |
| 4,944,734 A | 7/1990 | Wallach |
| 4,950,264 A | 8/1990 | Osborn, III |
| 5,006,394 A | 4/1991 | Baird |
| 5,007,894 A | 4/1991 | Enhorning |
| 5,074,855 A | 12/1991 | Rosenbluth et al. |
| 5,090,424 A | 2/1992 | Simon et al. |
| 5,131,906 A | 7/1992 | Chen |
| 5,263,947 A | 11/1993 | Kay |
| 5,312,384 A | 5/1994 | Temple |
| 5,336,208 A | 8/1994 | Rosenbluth et al. |
| 5,383,867 A | 1/1995 | Klinger |
| 5,386,836 A | 2/1995 | Biswas |
| 5,417,226 A | 5/1995 | Juma |
| 5,509,427 A | 4/1996 | Simon et al. |
| 5,513,659 A | 5/1996 | Buuck et al. |
| 5,589,978 A | 12/1996 | Fantone |
| 5,669,395 A | 9/1997 | Thompson |
| 5,693,002 A | 12/1997 | Tucker et al. |
| 5,804,215 A | 9/1998 | Cubbage et al. |
| 5,843,011 A | 12/1998 | Lucas |
| 5,877,216 A | 3/1999 | Place et al. |
| 6,131,575 A | 10/2000 | Lenker et al. |
| 6,179,775 B1 | 1/2001 | Thompson |
| 6,224,541 B1 | 5/2001 | Thompson |
| 6,461,340 B1 | 10/2002 | Lenker et al. |
| 6,593,313 B2 | 7/2003 | Place et al. |
| 6,836,684 B1 | 12/2004 | Rijkhoff et al. |
| 6,949,067 B1 | 9/2005 | Dann et al. |
| 6,964,643 B2 | 11/2005 | Hovland et al. |
| 7,565,198 B2 | 7/2009 | Bennett et al. |
| 8,684,008 B2 * | 4/2014 | St. Anne .............. A61F 2/0009 128/885 |
| 9,408,683 B2 | 8/2016 | St. Anne |
| 9,408,943 B2 * | 8/2016 | St. Anne .............. A61F 2/0009 |
| 9,492,260 B2 | 11/2016 | St. Anne et al. |
| D798,462 S | 9/2017 | St. Anne et al. |
| 2002/0055761 A1 | 5/2002 | Mann et al. |
| 2004/0242770 A1 | 12/2004 | Feldstein et al. |
| 2009/0118574 A1 | 5/2009 | Stephenson |
| 2011/0162661 A1 | 7/2011 | St. Anne |
| 2013/0184778 A1 | 7/2013 | St. Anne et al. |
| 2016/0339142 A1 | 11/2016 | St. Anne et al. |
| 2017/0281939 A1 | 10/2017 | St. Anne et al. |

OTHER PUBLICATIONS

"Incontinence—Urinary Leakage—A Common and Treatable Condition" Pamphlet, Kaiser Permanente (1995) in 11 pages.
"The selling of incontinence." Consumer Reports Oct. 1997 in 3 pages.
Document of record in the filed of parent U.S. Appl. No. 12/999,114 (now U.S. Pat. No. 8,684,008), filed Nov. 14, 2013 entitled "Activities of inventor Cora St. Anne described in the accompanying Information Disclosure Statement Transmittal submitted herewith on Nov. 14, 2013 in 6 pages."
Akala et al. "Novel pH-sensitive hydrogels with adjustable swelling kinetics." Biomaterials, Jun. 1998, 19(11-12) 1037-47.
Baron J: Partial androgen insensitivity syndrome: Ginekologia Polska, Jun. 1994, 65(6):319-25. (Abstract only) in 1 page.
Baron, J.: Classical and Incomplete Androgen Insensitivity Syndromes; Ginekologia Polska, Jul. 1994, 65 (7):377-86. (Abstract only) in 1 page.
Benzl JS: Vaginal dysfunction; in Benson JT (ed): Female Pelvic Floor Disorders. Norton, 1992, Chapter 13, pp. 307-311 in 5 pages.
Bond, SJ; Seibel, N; Kapur, S; Newman, KD: Rhabdomyosarcoma of the clitoris; Cancer, Apr. 1, 1994, 73(7):1984-6. (Abstract only) in 1 page.
Chalker et al. Overcoming Bladder Disorders. Harper and Row (1990) pp. 3, 44, and 45 in 3 pages.
Chapter 11, "Sphincter Electromyography and Other Electrophysiological Tests" in Hald et al.: The Urinary Bladder, Neurology and Dynamics; Williams & Wilkins (1982), pp. 118-127 in 10 pages.
Chapter 12, "Uroflowmetry and Pressure-flow Investigations" in Hald et al.: The Urinary Bladder, Neurology and Dynamics; Williams & Wilkins (1982), pp. 128-140 in 13 pages.
Chapter 13, "Urethral Closure Pressure Profile," in Hald et al.: The Urinary Bladder, Neurology and Dynamics; Williams & Wilkins (1982), pp. 141-150 in 10 pages.
Chapter 16, "Urinary Incontinence," in Hald et al.: The Urinary Bladder, Neurology and Dynamics; Williams & Wilkins (1982), pp. 175-203 in 29 pages.
Chapter 22, "Pitfalls and Errors in Urodynamic Assessment," in Hald et al.: The Urinary Bladder, Neurology and Dynamics; Williams & Wilkins (1982), pp. 310-329 in 20 pages.
Chapters 1 and 2 in Hald et al.: The Urinary Bladder, Neurology and Dynamics; Williams & Wilkins (1982), pp. ix-21 in 22 pages.
Chapters 3 and 4, pp. 22-47 of "The Urinary Bladder—Neurology and Dynamics," Lippincott (1982) in 28 pages.
Colleselli K et al. The female urethral sphincter: a morphological and topographical study. J Urology, Jul. 1998, 160 (1): 49-54. (Abstract only) in 1 page.
Dahms et al. "The impact of sacral root anatomy on selective electrical stimulation for bladder evacuation." World J. Urology, 1998, 16(5): 322-8 (Abstract only) in 1 page.
Dasgupta P; Haslam, C; Goodwin, R; Fowler, CJ; The 'Queen Square bladder stimulator': a device for assisting emptying of the neurogenic bladder: British Journal of Urology, Aug. 1997, 80(2):234-7. (Abstract only) in 1 page.
de Groat. Anatomy of the central neural pathways controlling the lower urinary tract. European Urology 1998, 34 Suppl. 1: 2-5 in 4 pages.
Deindl FM et al. "Dysfunctional voiding in women: which muscles are responsible?" British J. Urology, Dec. 1998, 82(6): 814-9 (Abstract only) in 1 page.
Deplanne et al. "The adrenergic, cholinergic, and NANC nerve-mediated contractions of the female rabbit bladder neck and proximal, medial and distal urethra." British J. Pharmacology, Apr. 1998 123(8): 1517-24 (Abstract only) in 1 page.
DETROL product literature (1999) in 62 pages.

(56) References Cited

OTHER PUBLICATIONS

Di Benedetto, V; Di Benedetto, A; Introduction of the anterior sagittal trans-ano-rectal approach (ASTRA) as a technical variation of the Passerini-Glazel clitoro-vaginoplasty; preliminary results; Pediatria Medica E. Chirurgica, Jul.-Aug. 1997, 19(4):273-6. (Abstract only) in 1 page.

El Hemaly, AK; Mousa, LA; Stress urinary incontinence, a new concept; European Journal of Obstetrics, Gynecology, and Reproductive Biology, Sep. 1996, 68(1-2):129-35. (Abstract only) in 1 page.

Female Pelvic Floor Disorders—Investigation and Management (Benson, J.T., ed.), Norton Medical Books (1992); Chapter 11C3 by B.C. Eriksen, Electrical Stimulation, pp. 219-231 in 15 pages.

Feneley, Roger C. L., "Normal Micturition and its Control" chapter in "Incontinence and its management," Croom Helm (1986) pp. 16-23 in 4 pages.

Fletcher, TF, Applied anatomy and physiology of the feline lower urinary tract. Veterinary Clinics of North America. Small Animal Practice, Mar. 1996, 26(2):181-96, Feb. 25, 1999 (Abstract only) in 1 page.

Fowler et al., Chapter 10, "Clinical Neurophysiology" in Torrens et al. "The Physiology of the Lower Urinary Tract," Springer-Verlag (1987) pp. 309-330 in 22 pages.

Franceschetti GP et al. Minimally invasive treatment of female urinary incontinence due to sphincter incompetence. Chirugia Italiana, 1998, 50(1): 17-24. (Abstract only) in 1 page.

Frauscher et al. Intraurethral ultrasound: diagnostic evaluation of the striated urethral sphincter in incontinent females. Eur. Radiol. 8, 50-53 (1998) in 4 pages.

Gartley. Managing Incontinence. Jameson Books (1985) p. 15 in 1 page.

Glavind K. Use of a vaginal sponge during aerobic exercises in patients with stress urinary incontinence. Int'l Urogynecology Journal and Pelvic Floor Dysfunction 1997; 8(6): 351-3 (Abstract only) in 1 page.

Gosling JA. "Modification of bladder structure in response to outflow obstruction and ageing." Euro. Urology, 1997, 32 Suppl 1: 9-14 (Abstract only) in 1 page.

Hajivassiliou. The development and evolution of artificial urethral sphincters. J. Med. Engineering and Technology, Jul.-Aug. 1998, 22(4): 154-9 (Abstract only) in 1 page.

Hale DS et al., Histologic analysis of needle biopsy of urethral sphincter from women with normal and stress incontinence with comparison of electromyographic findings. Am. J. Obstet. and Gyn, Feb. 1999, 180: 342-8 in 7 pages.

Hollander et al.: Pelvic floor neuropathy; in Benson JT (ed): Female Pelvic Floor Disorders. Norton, 1992, Chapter 11, pp. 195-198 in 14 pages.

Huang et al. Preservation of pudendal afferents in sacral rhizotomies. Neurosurgery, Aug. 1997, 41(2): 411-5 (Abstract only) in 1 page.

Incontinence: No Longer a Reason to Stay Home. Los Angeles Times Advertising Supplement Aug. 2, 1992 in 1 page.

INTROL Bladder Neck Support Prosthesis product literature. UroMed Corporation (1997) in 6 pages.

Jarvie et al. "Novel hydrophilic cyclic monomers in hydrogel synthesis." Biomaterials, Nov. 19, 1998, (21): 1957-61 (Abstract only) in 1 page.

Khullar V et al. The urethra (IPP, MUPP, instability, LPP). European Urology, 1998, 34 Suppl 1: 20-2. in 3 pages.

Kihara, K; de Groat, WC: Sympathetic efferent pathways projecting to the bladder neck and proximal urethra in the rat; Journal of the Autonomic Nervous System, Feb. 17, 1997, 62(3):134-42. (Abstract only) in 1 page.

Kouichi Ota, Tadao Yanagidani, Kazuhiro Kishikawa, Yuji Yamamori, and J.G. Collins: Cutaneous Responsiveness of Lumbar Spinal Dorsal Horn Neurons is Reduced by General Anesthesia, An Effect Dependent in Part on GAGA-A Mechanisms; J Neurophysiol. 80: 1383-1390, (1998) in 14 pages.

Larosa et al. Valsalva leak point-pressure (LPP) and maximal urethral closure pressure (MUCP) in women with stress urinary incontinence (SUI). Archivio Italiano di Urologia, Andrologia Dec. 1997, 69(5): 287-92 (Abstract only) in 1 page.

Li, P; Wilding, TJ; Kim, SJ; Calejesan, AA; Huettner, JE; Zhuo, M.:Kainate-receptor-mediated sensory synaptic transmission in mammalian spinal cord; Nature, Jan. 14, 1999, 397 (6715): 161-4. (Abstract only) in 1 page.

M. I. Resnick and A. C. Novick, "Urology Secrets" (1995) Chapter 42, pp. 133-138 in 6 pages.

McLennan et al. Supine empty stress test as a predictor of low valsalva leak point pressure. Neurology and Urodynamics 1998, 17(2): 121-7 (Abstract only) in 1 page.

Meyer et al. Stimulated pressure profile at rest: a noninvasive method for assessing urethral sphincter function. Urology Oct. 1998, 52(4): 679-84 (Abstract only) in 1 page.

Morrison, Chapter 4, "Sensations arising from the lower urinary tract" in Torrens et al. "The Physiology of the Lower Urinary Tract," Springer-Verlag (1987) pp. 89-131 in 43 pages.

Nagamatsu et al. Evaluation of clinical indexes to predict fate of pelvic nerve dysfunction. Urol. Res. 1998, 26: 319-23 in 5 pages.

National Association for Continence—Literature (1997) in 6 pages.

O'Connell et al. Anatomical relationship between urethra and clitoris. J. Urology Jun. 1998, 159(6) 1892-7. (Abstract only) in 1 page.

Olsen AL et al. Urethral sphincter needle electromyography in women: comparison of periurethral and transvaginal approaches. Neurourology and Urodynamics, 1998: 17(5) 531-5 (Abstract only) in 1 page.

Pacheco, P; Camacho, MA; Garcia, LI;Hernandez, ME; Carrillo, P; Manzo, J: Electrophysiological evidence for the nomenclature of the pudendal nerve and sacral plexus in the male rat; Brain Research, Jul. 25, 1997, 763(2):202-8. (Abstract only) in 1 page.

Park, K; Golstein, I; Andry, C; Siroky, MB; Krane, RJ; Azadzoi, KM: Vasculogenic female sexual dysfunction: the hemodynamic basis for vaginal engorgement insufficiency and clitoral erectile insufficiencey; International Journal of Impotence Research, Mar. 1997, 9(1):27-37. (Abstract only) in 1 page.

Prieto et al. Valsalva minimal leak point pressure: a useful approximation to type III urinary incontinence. Oct. 1998. 51(8) 783-9 (Abstract only) in 1 page.

Product Literature for the IMPRESS SOFTPATCH by UroMed Corporation (1998) in 12 pages.

Radziszewski P et al. "The morphological aspects of the innervation of the external urethral striated sphincter." Folia Morphologca, 1995, 54(1): 1-7 (Abstract only) in 1 page.

RELIANCE Urinary Control Insert product literature. UroMed Corporation (1997) in 8 pages.

Roan S. "Campaign Gets Info to Incontinent Women," Los Angeles Times, Apr. 6, 1997 p. E3 in 1 page.

Rocha et al. "Impact of Pregnancy and Childbirth on Female Rats' Urethral Nerve Fibers". J. International Urogynecology vol. 18 No. 12 (2007) (Abstract only) in 1 page.

Salansky, N; Fedotchev, A; Bondar, A: Responses of the venous system to low frequency stimulation and EEG rhythms: clinical implications; Neuroscience and Biobehavioral Reviews, May 1998, 22(3); 395-409. (Abstract only) in 1 page.

Siltberg et al. Cough-induced leak-point pressure. Acta Obstet Gynecol Scand 77 (1998): 1000-1007 in 8 pages.

Statutory Invention Registration (SIR) No. H1602 to Brock published Oct. 1, 1996 in 8 pages.

Steg. "Urinary Incontinence", p. 266 Churchill Livingstone (1992) in 1 page.

Strohbehn, K; Quint, LE; Prince, MR; Wojno, KJ; Delancey, JO; Magnetic resonance imaging anatomy of the femal urethra: a direct histologic comparision; Obstetrics and Gynecology, Nov. 1996, 88(5):750-6. (Abstract only) in 1 page.

Tan et al. Female pelvic floor: endovaginal MR imaging of normal anatomy. Radiology Mar. 1998, 206(3) 777-83 (Abstract only) in 1 page.

Torrens, Chapter 9, "Urodynamics" in Torrens et al. "The Physiology of the Lower Urinary Tract," Springer-Verlag (1987) pp. 277-305 in 29 pages.

(56) References Cited

OTHER PUBLICATIONS

Uher et al. "Sacral reflexes: physiology and clinical application." Dis. Colon and Rectum, Sep. 1998, 41(9): 1165-1177 (Abstract only) in 1 page.

Urinary Incontinence in Adults, National Institutes of Health Consensus Development Conference Statement (1988) in 18 pages.

Urinary Stress Incontinence—Awareness Encourages Women to Speak Up, Seek Help (1993), Daniel Freeman Memorial Hospital, in 1 page.

USA Weekend HealthSmart "Can I gain control?—Effective new therapies make living with incontinence easier." p. 14 (2006) in 1 page.

van Buren. "No One Needs to Live with Incontinence," Los Angeles Times, Apr. 6, 1997 p. E4 in 1 page.

Van Duin et al., A computer model of the neural control of the lower urinary tract. Neurourology and Urodynamics, 1998, 17(3): 175-96. (Abstract only) in 1 page.

Von Heyden et al. Neurotransmitters in the human urethral sphincter in the absence of voiding dysfunction. Urol. Res. (1998) 26: 299-310 in 13 pages.

Walker, RJ; Brooks, HL; Holden-Dye, L: Evolution and Overview of Classical Transmitter Molecules and Their Receptors; Parasitology, 1996, 113 Suppl: S3-33. (Abstract only) in 1 page.

Wang et al. Tension-free vaginal tape. A minimally invasive solution to stress urinary incontinence in women. J. Reprod. Med. May 1998, 43(5): 429-34 (Abstract only) in 1 page.

Warrell DW: Pelvic floor neuropathy; in Benson JT (ed): Female Pelvic Floor Disorders. Norton, 1992, Chapter 9, pp. 153-165 in 13 pages.

White R. Incontinence. Encyclopedia Brittanica 1985 Medical and Health Annual pp. 335-338 in 4 pages.

Wyczolkowski M. Functional evaluation of the internal urethral sphincter in transrectal USG. Przeglad Lekarski, 1998, 55(3): 128-32. (Abstract only) in 1 page.

Yilmaz et al. Clitoral Electromyography. J. Urology 167 2:1 (2002) (Abstract only) in 2 pages.

International Search Report for PCT/US2010/033349 dated Jan. 11, 2011 in 6 pages.

\* cited by examiner

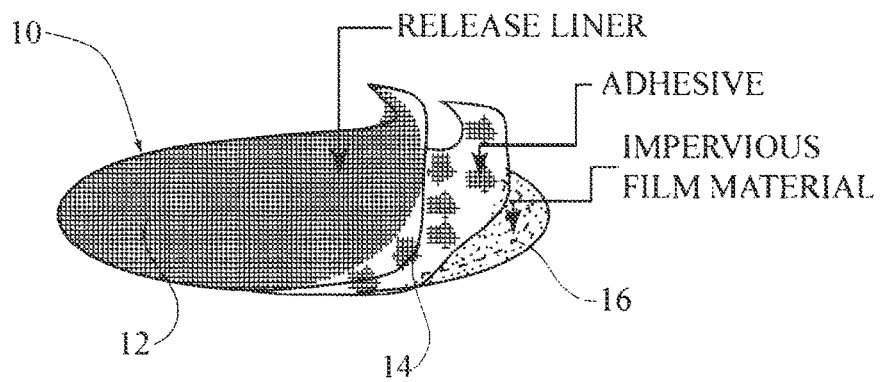
Fig. 1
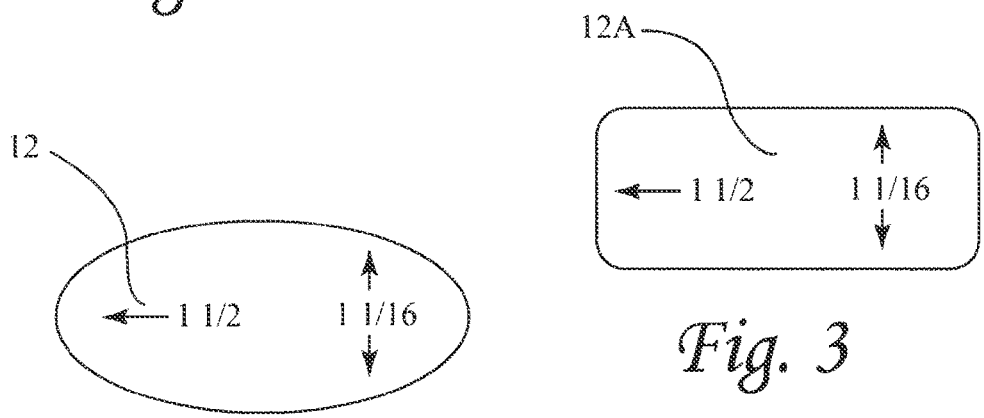
Fig. 2
Fig. 3
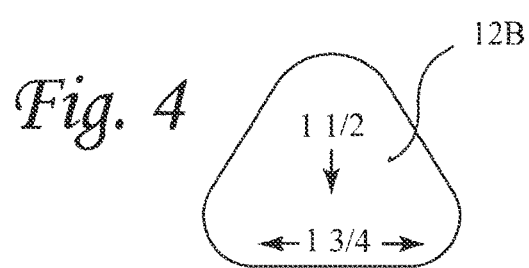
Fig. 4

METHOD AND DEVICE FOR TREATING FEMALE PELVIC NERVE DYSFUNCTION

CROSS-REFERENCE TO RELATED APPLICATIONS

This application is a continuation-in-part of application Ser. No. 12/999,114 filed under 35 U.S.C. § 371 on Mar. 23, 2011, now U.S. Pat. No. 8,684,008, which is a national stage application of PCT Application Serial No. PCT/US10/33349 filed on May 3, 2010, which claimed the benefit of U.S. Provisional Patent Application No. 61/181,556 filed May 27, 2009, all of which applications are hereby incorporated by reference in their entireties.

FIELD OF THE INVENTION

The invention relates to a method and device for relieving or mitigating the problems associated with female urinary frequency and urgency with or without urinary incontinence.

BACKGROUND OF THE INVENTION

"Over active bladder" is defined by the International Incontinence Society as a "symptom syndrome suggestive of lower urinary tract dysfunction." It is specifically defined as "urgency, with or without urge incontinence, usually with frequency and nocturia." Female overactive bladder is a troublesome problem for many individuals. The condition may result from involuntary contraction of the bladder muscle. A number of prescription drugs are used with limited success in treating an overactive bladder and have significant side effects. Other treatments include dietary modification, Kegel instructions and formal physical therapy and different forms of electrical neuromodulation to affect the bladder reflux arc. For those whom these therapies cannot help, there are management modalites of absorbent pads that are used to collect leakage.

A number of devices have been proposed to deal with female urinary incontinence, represented by, for example, U.S. Pat. No. 5,074,855 to Rosenbluth et al., U.S. Pat. No. 6,131,575 to Lenker et al., U.S. Pat. No. 6,461,340, to Lenker et al., U.S. Pat. No. 3,789,828 to Schulte, U.S. Pat. No. 5,509,427 to Simon et al. U.S. Pat. No. 4,892,535 to Björnberg et al., U.S. Pat. No. 6,179,775 to Thompson, U.S. Pat. No. 6,836,684 to Rijkhoff, and Statutory Invention Registration (SIR) No. H1602 to Brock, the disclosures of each of which are hereby incorporated herein by reference.

Rosenbluth et al. and both Lenker et al. patents disclose a resilient pad configured to seal against and occlude the urethral meatus, i.e., the urethral opening. These devices are described as shaped and sized to fit each individual user's anatomy, implying that the application of this device requires careful attention for a comfortable fit. Moreover, the devices are designed for individual custom fitting, calling for predetermined sizes to be trimmed individually for optimal fit, including the use in some cases of a mold of the relevant portions of the vulva taken prior to sizing the pad. A mirror or light is suggested to facilitate insertion, indicating that the devices are difficult to apply and suggests that the device may be designed for clinical use, attended by a physician or health care professional. Moreover, these devices do not appear to be optimally designed for highly active women, e.g. running, jogging, high and low impact aerobics or any exercise where the movement of the lower torso is integral. The devices are rigid around the perimeter contributing to discomfort as used in its intended position. In addition, the complex construction and individual custom fitting indicates a probable high overall cost to the consumer.

Lenker et al. U.S. Pat. No. 6,131,575 discloses in addition to the rigid female incontinence device, a more flexible device but only for male incontinence, shown in their FIGS. 26 to 30, and which is retained on the glans of a patient's penis by an adhesive layer formed of a pressure-sensitive hydrophilic hydrogel.

The device described in Shulte's patent is a mechanical device surgically implanted for prolonged use and features a fluid flow valve which can be operated manually, in contrast to the present invention's simplicity, ease of use and temporary nature as needed at the discretion of the user. In structure, the Shulte device appears to be a rigid mechanical device with a valve. Simon et al.'s device is designed to be inserted directly inside of the urethra with an "expandable balloon at its proximal end," again, which is in total contrast to our present invention. Björnberg et al. and Brock describe absorbent pads of the type that can be used as incontinence pads. Brock further describes a continuous layer of adhesive for securing the pad to a wearer's skin. The pads of both Björnberg et al. and Brock are intended to cover large general areas.

Thompson describes a device to enhance clitoral stimulation during intravaginal intercourse, using a hydrophilic, non-allergenic adhesive to seat a foraminous, elongated, generally triangular shaped pad in the female vestibule to lie beneath the labia minora to support and engage the ventral aspect of the clitoris when it is engorged with blood during the arousal phase of female sexual stimulation.

Rijkhoff et al. describes a device that uses an implanted sensor and means for generating electrical pulses to stimulate nerves to inhibit contraction of the detrusor, the muscle that expels urine from the bladder. It recognizes what has been shown by investigators, that activation of afferent nerve fibres, innervating mechanoreceptors located in the clitoris, has a strong inhibitory effect on the bladder.

BRIEF SUMMARY OF THE INVENTION

The present invention provides a method and devices for treating a pelvic condition by stimulating visceral pelvic or somatic nerves or their pathways of a female person suffering from a pelvic condition of nerve dysfunction. A non-electrical, external physical stimulation is applied to the clitoral region of the person. Such stimulation is believed to result in neuromodulation. The pelvic condition of nerve dysfunction can include female urinary frequency or urgency, overactive bladder, urinary incontinence or retention, fecal incontinence, constipation, interstitial cystitis, or pelvic pain, such as vulvadynia.

There is evidence that the clitoris with its hood is innervated by the parasympathetic visceral efferent and afferent fibres that arise from the sacral center (S2-S4), and possibly also the sympathetic preganglionic afferent and visceral efferent fibres from the thorocolumbar centre (T11-L2), which can help to explain the beneficial effect on the bladder, urethra and other pelvic structures such as the colon, which have similar innervations. Notwithstanding the ability to provide such complete relief, the device is remarkably simple. Unlike prior devices, it is not an absorbent pad to catch urine or trap urine in the bladder (like Lenker et al. U.S. Pat. No. 6,131,575), it is not a clinical device that requires help for insertion into the body, it does not have a rigid or semi-rigid component, nor does it have projections, and is not a complicated electronic impulse generator. Moreover, the device can be used in the presence of intercourse.

In accordance with the present invention, external stimulation is applied to the clitoral region, for example, the clitoral hood, by a substance adapted to be secured over the clitoral region. In one embodiment, the substance comprises a patch with adhesive and is applied to the clitoral region. Traction provided by the patch is sufficient to stimulate the nerves of the clitoral region. The adhesive can be on both or either side of a backing sheet formed of a flexible material. The flexible material can have a thickness of from about 0.012 mm to about 0.051 mm with an adhesive layer on a backing sheet, the adhesive layer being suitable for application directly to the clitoral region, the patch being shaped so as to cover the clitoral region. A release sheet can be provided to protect the adhesive layer from drying out before use. In another embodiment, the patch has adhesive on one side of a backing sheet. A plurality of such patches can be arranged linearly, connected by tear lines. Optionally, a small cloth or paper tab can be secured by the adhesive at a leading edge of the patch to facilitate handling The linear arrangement of patches can be mounted in a dispenser so configured so that single patches can be withdrawn from the dispenser aided by pulling on the tab, which also serves to act as a stop in drawing the patch from the dispenser.

In another embodiment, a solid object, which can be pliable, is secured against the clitoral region. The solid object, for example a solid curvilinear plastic member can be secured to the front side of a backing sheet having an adhesive layer on the front side whereby the solid object can be applied directly to the clitoral region to apply physical pressure thereon. Other shapes can be used.

In still another embodiment, the solid object can be mounted on the inside of a supportive garment, such as a panty, in a location such that in wearing the panty, the solid object will be applied to the clitoral region to apply physical pressure thereon.

The present invention provides a simple, low cost solution to a vexing problem, making therapy more safe, affordable and available. It is designed to comfortably fit almost any human female who suffers from urinary frequency or urgency and includes the necessary elements that compliment comfort, ease of use and confidence. The patch, for example, is produced with soft, pliable materials that allow the user to continue daily routines with no discomforts or embarrassing interruptions. With the possible exception of a disabled person requiring assisted living, who would have the device applied by someone else, the present invention is designed to permit the user to apply the device without any assistance.

The device can be produced in various sizes, e.g. small, medium, and large to accommodate the over-the-counter market. It is well suited for minimally active to highly active women, e.g. engaging in running, jogging, high or low impact aerobics or any exercise where movement of the lower torso is essential. The product is very portable and can be available in individually sealed and sterilized packages of multiple units, which can easily fit into the average purse or pouch. The cost, comfort, simplicity, portability and ease of use attributed to this device, surpass all other products presently available in the consumer's over-the-counter market.

BRIEF DESCRIPTION OF THE DRAWINGS

For a more complete understanding of the present invention, reference is now made to the following descriptions taken in conjunction with the accompanying drawing, in which:

FIG. 1 is a perspective view of the device, in which this embodiment having an oval shape, shown with portions peeled up to better illustrate its construction;

FIG. 2 is a top plan view of the device of FIG. 1;

FIG. 3 is a top plan view of the device of FIG. 1, but having a rectangular shape;

FIG. 4 is a top plan view of a device similar to the device of FIG. 1, but having a triangular shape;

DETAILED DESCRIPTION OF THE INVENTION

Figure 5:
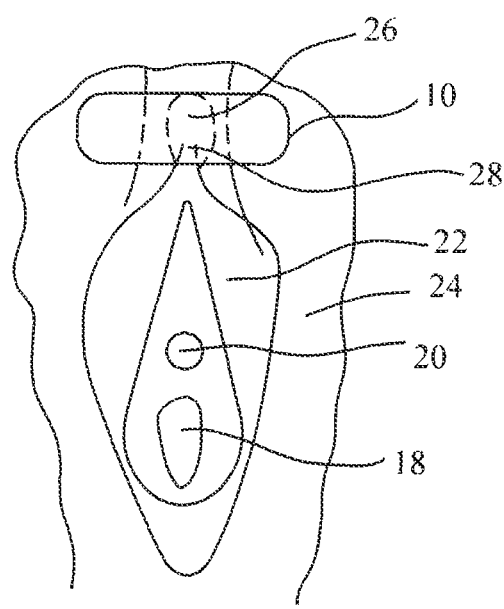
FIG. 5 is a sketch of a vagina illustrating components relevant to the invention and showing application of the patch to the clitoral hood.

Referring to FIGS. 1 and 2, a generally oval patch 10 of this invention is shown formed of a backing sheet 16 coated with a layer of adhesive 14 and covered with a release sheet/layer 12. The adhesive layer 14 is preferably pressure sensitive and non-allergenic, as known to the art. The patch is approximately 1⅞ inches long and 1¹⁄₁₆ inches wide at its widest.

The backing sheet 16 is a film material and is preferably manufactured from a thin, flexible plastic film, although other flexible liquid materials may also be used. As used herein, the term "flexible" refers to materials which are compliant and will readily conform to the general shape and contours of clitoris region. The backing sheet 16 material may as described for the backsheet material of Statutory Invention Registration (SIR) No. H1602 to Brock, incorporated herein by reference, and can comprise a woven or nonwoven material, polymeric films such as thermoplastic films of polyethylene or polypropylene, or composite materials such as a film-coated nonwoven material, illustrated by a polyethylene film having a thickness of from about 0.012 mm to about 0.051 mm.

The release layer/sheet 12 keeps the adhesive from drying out and can be formed of an adhesive releasing material, as known by the art, and as also illustrated in Brock SIR No. H1602. Other non-limiting examples of the adhesive releasing material/sheet includes paper, resin film, nonwoven fabric, and nonwoven fabric laminated with resin film, each having been treated with silicon. The release layer is removed before applying the patch 10.

The adhesive layer can comprise of a hydrophilic adhesive composition which may be sticky, viscous gel, or a substantially solid composition. The adhesive layer can also comprise of pressure sensitive adhesives (PSA) made from polymer such as acrylic and methacrylic ester homo or copolymers, butyl rubber-based systems, silicones, urethanes, vinyl esters and amides, olefin copolymers, butyl rubber-based or synthetic rubbers and the like. In another embodiment, the adhesive layer can comprise of bioadhesives (Bas) as known to the art. In contrast to PSAs that adhere mainly to dry substrates, Bas exhibit good tack when adhered to hydrated biological substrates/tissues. Non-limiting examples includes slightly cross-linked polyacrylic and polymethacrylic acids as well as blends of hydrophilic cellulose derivatives (40-95%) with polyethylene glycol. In other embodiments, the adhesive layer can comprise different combinations of PSA and BA polymeric materials of different hydrophilicity and thus different solubilities in water or in the liquids secreted by the tissue region in contact with the adhesive layer.

Regardless of the adhesive composition used, the final adhesive layer should preferably be pressure sensitive, hydrophilic and non-allergenic.

FIG. 3 shows a patch 10A constructed in the same manner as the patch of FIG. 1, but having a generally rectangular shape 1½ inches long and 1 and ¹⁄₁₆ inches wide.

FIG. 4 shows a patch 10B constructed in the same manner as the patch of FIG. 1, but having a generally triangular shape 1½ inches high and 1 and ¾ inches at its base.

The patch 10 is applied with the adhesive layer directly on the clitoral region. FIG. 5 is a sketch of a vagina illustrating relevant components of a vagina, including the vaginal opening 18, the urethral opening 20, the labia minora 22, the labia majora 24, the clitoral hood 26 and the clitoris at 28. In this embodiment, the patch 10 is applied solely to the clitoral region by being applied to the clitoral hood 26. The adhesive layer 14 physically stimulates the clitoral nerves 28 to provide a strong inhibitory effect on the bladder, relieving urinary urgency and frequency.

Figure 6:
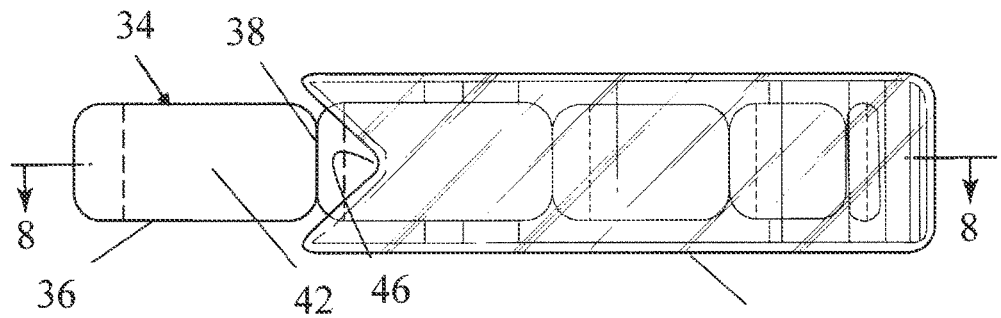
FIG. 6 is a top view of a transparent dispenser showing a plurality of patches arranged linearly and connected by tear lines.
Figure 7:
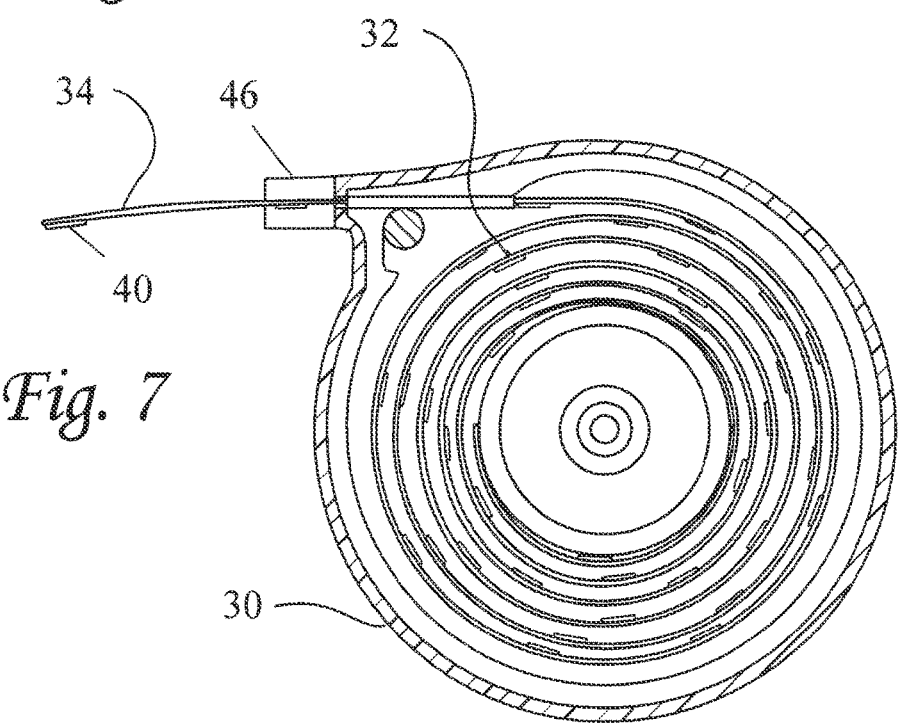
FIG. 7 is a cross-sectional view of the dispenser of FIG. 7.
Figure 8:
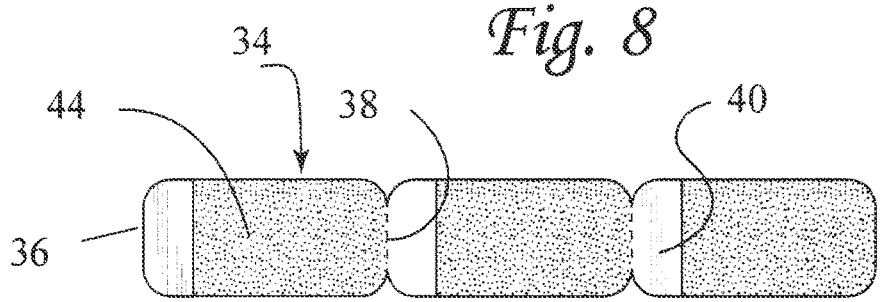
FIG. 8 shows the underside of three of the plurality of patches contained in the dispenser of FIG. 7, connected by tear lines.
Figure 9:
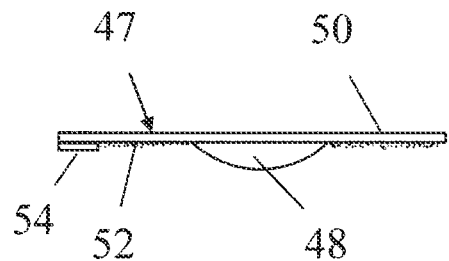
FIG. 9 shows a patch to which a solid, curvilinear object is secured to the front side of a backing sheet having an adhesive layer on said front side.

While a single patch 10 is shown in FIG. 1, in actual production and for sale, a plurality of such patches may be formed on a single release sheet and sold as a kit whereby individual patches can be removed and applied as needed. FIGS. 6, 7 and 8 show an embodiment in which a dispenser 30 is provided containing a roll 32 of a linearly arranged array 34 of patches 36. Referring specifically to FIG. 8, the undersides of three patches 36 of the linear patch array 34 are shown. The patches 36 are connected by tear lines 38 and have a paper or cloth tab 40 on each end. Each patch has a backing sheet 42 (FIG. 7) and an adhesive layer 44 (FIG. 9). The tab 40 is secured to the underside of the patch by the adhesive layer 44.

In operation, one grasps the tab end of a patch extending from the mouth 46 of the dispenser, pulling it until the tab 40 of the next patch is momentarily stopped by the closeness of the dispenser mouth 46. The withdrawn patch is then torn from the array along its tear line 38.

Referring to FIG. 9, a patch 47 is shown in which a solid but pliable curvilinear object 48 is secured to the underside of a backing sheet 50 having an adhesive layer 52 on the patch underside which carries the solid object 48 as well as a paper or cloth tab 54. The device of FIG. 9 can be carried as a linear array, separated by tear lines in the manner of the patches 35 of FIGS. 6-8 by the dispenser 30. A separated patch is applied directly to the clitoral region, over the hood, to apply physical pressure on the clitoral region. Other shapes for the solid object can be provided, such as a spherical shape, or the like.

Figure 10:
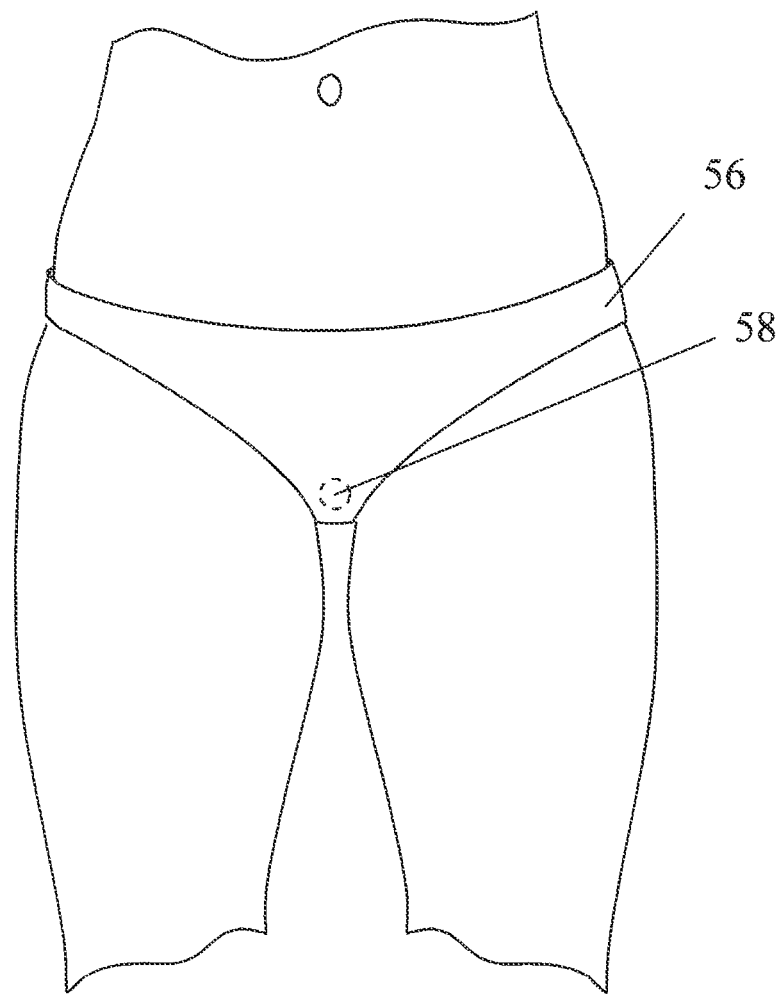
FIG. 10 shows a supportive garment, in this case a panty, having a solid object mounted therein so as to be applied to the clitoral region to apply physical pressure thereon.

Referring to FIG. 10, a panty 56 is shown having a solid object 58, which can be the solid object 48 of FIG. 9, mounted therein, such as by adhesive or sewing, so as to be applied to the clitoral region, over the hood, to apply physical pressure thereon The patches described herein enable the stimulation of the visceral pelvic or somatic nerves or their pathways of a female person suffering from a pelvic condition of nerve dysfunction. The invention applies a non-electrical, external physical stimulation to the clitoral region. As discussed in the summary of the Invention, such stimulation is believed to result in neuromodulation. The pelvic condition of nerve dysfunction can include female urinary frequency or urgency, overactive bladder, urinary incontinence or retention fecal incontinence, constipation, interstitial cystitis, or pelvic pain, such as vulvadynia.

The following examples further illustrate the invention.

Example 1

A patient suffering from female urinary incontinence can be given a dispenser of FIG. 6 with instructions to tear a section containing a patch along the line of weakness and apply it over the clitoral hood to relieve the urinary incontinence. For as long as the incontinence continues, a new patch should be applied each day and after each shower or bath. The patch will serve to stimulate the visceral pelvic or somatic nerves or their pathways pelvic to treat nerve dysfunction. No adverse side effects would be suffered.

Example 2

The procedure of Example 1 can be followed to provide relief from any of the following conditions: urinary frequency or urgency, overactive bladder, urinary retention, fecal incontinence, constipation, interstitial cystitis, or vulvadynia to stimulate the visceral pelvic or somatic nerves or their pathways pelvic to treat nerve dysfunction. No adverse side effects would be suffered.

Example 3

A patient suffering from female urinary frequency cr urgency, overactive bladder, urinary incontinence or retention, fecal incontinence, constipation, interstitial cystitis, or vulvadynia can be given a patch such as shown in FIGS. 6-8 with instructions to apply it over the clitoral hood. For as long as the incontinence continues, a new such device should be applied each day and after each shower or bath. The device will serve to stimulate the visceral pelvic or somatic nerves or their pathways to treat nerve dysfunction. No adverse side effects would be suffered.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. A device adapted for providing an inhibitory effect on a bladder of a female person, comprising a patch having a substantially planar skin-contacting surface and sized and configured to be secured directly over and covering a clitoris without covering a urethra of said person, the patch formed of a backing sheet of flexible material with an adhesive layer comprising an adhesive on one side of the backing sheet, the adhesive layer removably connected to a release layer, the patch configured when applied to stimulate the clitoris to inhibit bladder discharge.

2. A kit comprising a plurality of patches as in claim 1, whereby individual patches can be removed and applied.

3. The kit of claim 2, wherein the patches are arranged in linear form and provided with lines of weakness or perforations sufficient to permit each patch to be torn away from the other patches.

4. The device of claim 1, in which the patch includes a tab on one end to facilitate holding the patch.

5. The device of claim 1, wherein the adhesive comprises a pressure-sensitive adhesive.

6. The device of claim 1, wherein the adhesive comprises a silicone adhesive.

7. The device of claim 1, wherein the adhesive comprises a bioadhesive.

8. The device of claim 1, wherein the patch comprises a generally rectangular shape.

9. The device of claim 1, wherein the patch comprises a generally triangular shape.

10. The device of claim 1, wherein the patch has a length of approximately 1½ inches and a width of approximately 1 1/16 inches.

11. The device of claim 1, wherein the adhesive is hydrophilic.

12. The device of claim 1, wherein the device is configured to treat urinary incontinence.

13. The device of claim 1, wherein the patch comprises a generally arcuate shape.

14. A method for creating an inhibitory effect on a bladder, comprising applying a flexible patch having a substantially planar skin-contacting surface directly to a clitoris of a person thereby covering the clitoris, the patch comprising an adhesive, wherein applying the patch does not comprising covering a urethra of the person with the patch.

15. The method of claim 14, wherein the person suffers from urinary incontinence.

16. The method of claim 14, further comprising removing a release layer operably attached to the adhesive from the patch prior to applying the patch to the clitoris.

17. The method of claim 14, wherein the patch when applied provides traction sufficient to stimulate a nerve of the clitoris.

18. The method of claim 14, wherein applying the patch to the clitoris comprises applying the patch to the clitoral hood.

19. The method of claim 14, wherein the applying the patch step is performed by the person.

20. The method of claim 14, wherein the method also treats one or more of the following conditions selected from the group consisting of: fecal incontinence, constipation, interstitial cystitis, and vulvadynia.

* * * * *